United States Patent
Johnson et al.

(10) Patent No.: US 10,031,100 B2
(45) Date of Patent: Jul. 24, 2018

(54) GENERATION OF PH/TEMPERATURE/IONIC GRADIENTS ON A LATERAL FLOW PLATFORM WITH MULTIPLE PARALLEL LANES FOR MODULATING PROTEIN INTERACTIONS

(71) Applicant: Robert Bosch GmbH, Stuttgart (DE)

(72) Inventors: Christopher Johnson, Mountain View, CA (US); Sam Kavusi, Menlo Park, CA (US); Habib Ahmad, Sunnyvale, CA (US); Christoph Lang, Cupertino, CA (US)

(73) Assignee: Robert Bosch GmbH, Stuttgart (DE)

( * ) Notice: Subject to any disclaimer, the term of this patent is extended or adjusted under 35 U.S.C. 154(b) by 995 days.

(21) Appl. No.: 13/800,328

(22) Filed: Mar. 13, 2013

(65) Prior Publication Data

US 2014/0274754 A1 Sep. 18, 2014

(51) Int. Cl.
*G01N 33/558* (2006.01)
*G01N 33/543* (2006.01)
*G01N 27/327* (2006.01)
*B01L 3/00* (2006.01)

(52) U.S. Cl.
CPC ........ *G01N 27/3276* (2013.01); *B01L 3/5027* (2013.01); *G01N 33/5438* (2013.01); *G01N 33/558* (2013.01); *B01L 2300/069* (2013.01); *B01L 2300/0636* (2013.01); *B01L 2300/0645* (2013.01); *B01L 2300/089* (2013.01); *B01L 2400/0406* (2013.01)

(58) Field of Classification Search
CPC ............ G01N 33/5438; G01N 33/558; G01N 27/3276; B01L 2300/0636; B01L 2300/0645
See application file for complete search history.

(56) References Cited

U.S. PATENT DOCUMENTS

| | | | | |
|---|---|---|---|---|
| 5,354,538 A | * | 10/1994 | Bunce ..................... | B01L 3/502 422/520 |
| 5,837,546 A | * | 11/1998 | Allen ................. | G01N 33/5438 422/403 |
| 6,413,394 B1 | * | 7/2002 | Shen .................. | G01N 33/5438 204/403.02 |
| 6,444,461 B1 | * | 9/2002 | Knapp .................. | B01L 3/0262 204/450 |
| 6,656,745 B1 | * | 12/2003 | Cole ................ | G01N 33/54386 422/408 |

(Continued)

FOREIGN PATENT DOCUMENTS

| | | |
|---|---|---|
| CN | 102822674 | 12/2012 |
| JP | 2001508180 | 6/2001 |

(Continued)

OTHER PUBLICATIONS

U.S. Appl. No. 13/543,300, filed Jan. 9, 2014, Kavusi et al.
U.S. Appl. No. 13/658,614, filed Apr. 24, 2014, Kavusi et al.
International Search Report dated Aug. 28, 2014 of the corresponding International Application PCT/US2014/024760 filed Mar. 12, 2014.

(Continued)

*Primary Examiner* — Scott Long
*Assistant Examiner* — Gary E Hollinden
(74) *Attorney, Agent, or Firm* — Gerard Messina (57) ABSTRACT

Lateral flow assay devices for determining the concentration of a biomolecular analyte in a sample and methods for measuring analyte concentration in sample using such lateral flow assay devices.

19 Claims, 4 Drawing Sheets

(56) References Cited

U.S. PATENT DOCUMENTS

| | | | |
|---|---|---|---|
| 8,071,319 B2* | 12/2011 | Metzger | B82Y 5/00 |
| | | | 435/7.2 |
| 9,075,041 B2* | 7/2015 | Kavusi | G01N 33/50 |
| 9,731,297 B2* | 8/2017 | Glezer | B01L 7/525 |
| 2003/0068665 A1 | 4/2003 | Kawamura et al. | |
| 2003/0103869 A1* | 6/2003 | Hardman | B01L 3/5023 |
| | | | 436/518 |
| 2007/0031283 A1* | 2/2007 | Davis | A61B 5/14546 |
| | | | 422/400 |
| 2007/0148039 A1 | 6/2007 | Padmanabhan et al. | |
| 2009/0325276 A1* | 12/2009 | Battrell | B01F 11/0071 |
| | | | 435/287.2 |
| 2010/0194409 A1* | 8/2010 | Gao | C12Q 1/6825 |
| | | | 324/693 |
| 2010/0285601 A1* | 11/2010 | Kong | G01N 33/54306 |
| | | | 436/94 |
| 2011/0091870 A1 | 4/2011 | Lang et al. | |
| 2011/0117540 A1* | 5/2011 | Cary | C12N 15/101 |
| | | | 435/5 |
| 2011/0124130 A1* | 5/2011 | Wagner | G01N 33/54366 |
| | | | 436/518 |
| 2011/0195853 A1 | 8/2011 | Kavusi et al. | |
| 2012/0028822 A1 | 2/2012 | Joseph et al. | |
| 2012/0042722 A1* | 2/2012 | Song | G01N 33/558 |
| | | | 73/32 R |
| 2012/0288961 A1* | 11/2012 | Yager | B01L 3/5023 |
| | | | 436/501 |
| 2013/0260481 A1 | 10/2013 | Shimizu et al. | |
| 2017/0080420 A1* | 3/2017 | Lowe | B01L 3/502715 |

FOREIGN PATENT DOCUMENTS

| | | |
|---|---|---|
| JP | 2003161733 | 6/2003 |
| JP | 2008541017 | 11/2008 |
| JP | 2013508682 | 3/2013 |
| WO | 98/32018 | 7/1998 |
| WO | 2006/119203 | 11/2006 |
| WO | WO2008/147382 | 12/2008 |
| WO | 2011/047020 | 4/2011 |
| WO | WO2012/081361 | 6/2012 |

OTHER PUBLICATIONS

Geertruida A. Posthuma-Trumpie et al., "Lateral flow (immune) assay: its strengths, weaknesses, opportunities and threats. A literature survey", Analytical and Bioanalytical Chemistry, Springer, Berlin, DE, vol. 393, No. 2, Aug. 13, 2008, pp. 569-582.

Adeyabeba Abera and Jin-Woo Choi: "Quantitative lateral flow immunosensor using carbon nanotubes as label", Anaytical Methods, Royal Society of Chemistry, GBR, vol. 2, No. 11, Nov. 1, 2010, pp. 1819-1822.

\* cited by examiner

GENERATION OF PH/TEMPERATURE/IONIC GRADIENTS ON A LATERAL FLOW PLATFORM WITH MULTIPLE PARALLEL LANES FOR MODULATING PROTEIN INTERACTIONS

FIELD OF THE INVENTION

The invention relates to a device for Lateral Flow (LF) assays as a biosensor, methods of improving such LF assay device, and using such LF assay device in a diagnostic method.

BACKGROUND INFORMATION

Recently there has been an increased interest in predictive, preventative, and particularly personalized medicine which requires diagnostic tests with high reproducibility, sensitivity and specificity. Lateral Flow (LF) assay devices incorporate such diagnostic test and are a well-established technology in Point-of-Care (POC) diagnostics. When compared with other diagnostic techniques such as ELISA and PCR/Q-PCR, LF assay devices have the advantage of being rapid, simple, largely automated, and cost effective. Relative ease of manufacture, long shelf life, and ease of use by the customer are some further advantages that make LF assay devices very attractive.

LF assay devices are often used as diagnostic devices where the main focus is on qualitative systems which provide an easy yes or no answer. Currently however, there is an increasing demand for more sensitive, quantitative and also multiplexing measurements which require the implementation of reader systems.

The most common sensing method used in LF assay devices is optical sensing, often by visual inspection, to detect a colorimetric, fluorescent or other visual change as a result of the assay. Reagent labels used to achieve such change include colloidal gold, latex particles, carbon, fluorescent molecules, and chemiluminescent molecules. Enzymatic reactions can be applied subsequently to amplify the signal. The main problems associated with visual detection of labels are: the relatively poor limits of detection in the absence of amplification, the inability to obtain kinetic information from the assay, and the lack of quantitative information gained from the assay. There is a distinct need for alternatives to visual characterization that can provide quantitative real time analysis while maintaining the simple, rapid, cost effective device that makes LF tests so appealing.

Figure 1:
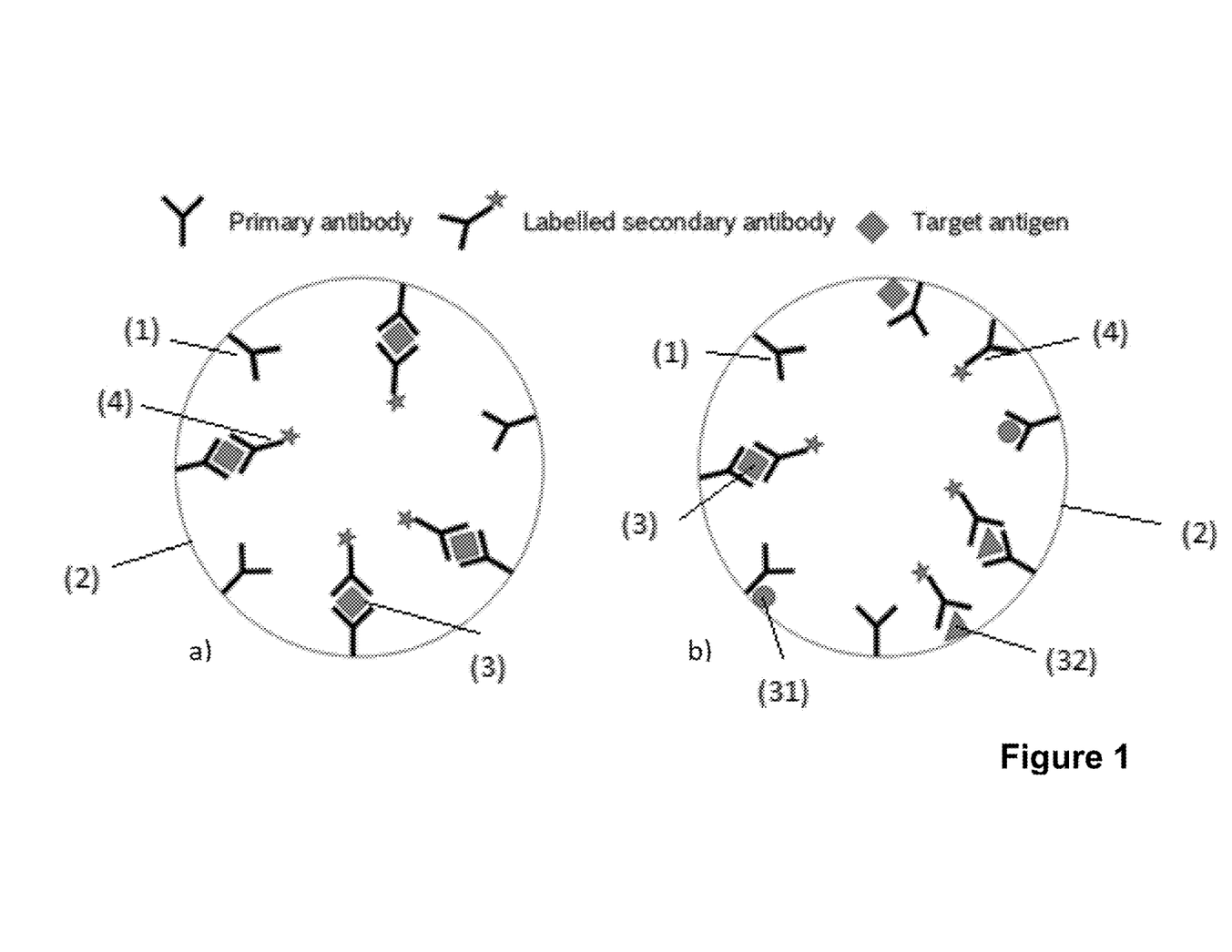
FIG. 1: An illustration of the cross reactivity problem. Diagram a) shows the ideal scenario where no cross reaction occurs and all the signal is a result of specific interactions. Diagram b) shows molecules other than the antigen of interest (diamond) can bind to primary antibody or the surface and either create incorrect signal or prevent the antigen in forming a sandwich.

Ideally LF tests are run directly with a patient sample, without the need for purification, as this reduces the time, complexity and cost associated with processing prior to analysis. Unfortunately, the large variety of biomolecules in a raw sample increases the chance of nonspecific cross reactivity within the assay, which can cause a false positive reading as illustrated in FIG. 1. While this can be prevented through development of better, more specific, probe molecules, the development process thereof is expensive and laborious and is not guaranteed to eliminate cross-reactivity completely. However, it is well known that reaction kinetics and binding strengths differ between specific and non-specific binding interactions. Furthermore, these binding characteristics are susceptible to change through local environmental factors including temperature, pH, and ionic strength. By controllably varying local environmental parameters, it is possible to better characterize a detected interaction as either specific or non-specific.

Some other key factors that affect the signal produced in a LF assay device include temperature and ionic strength (including pH) of the solution or local environment. Including sensors and actuators that measure and influence such conditions allows for controllably varying the local environmental parameters in order to provide a more accurate qualitative and/or quantitative diagnostic device.

Figure 2:
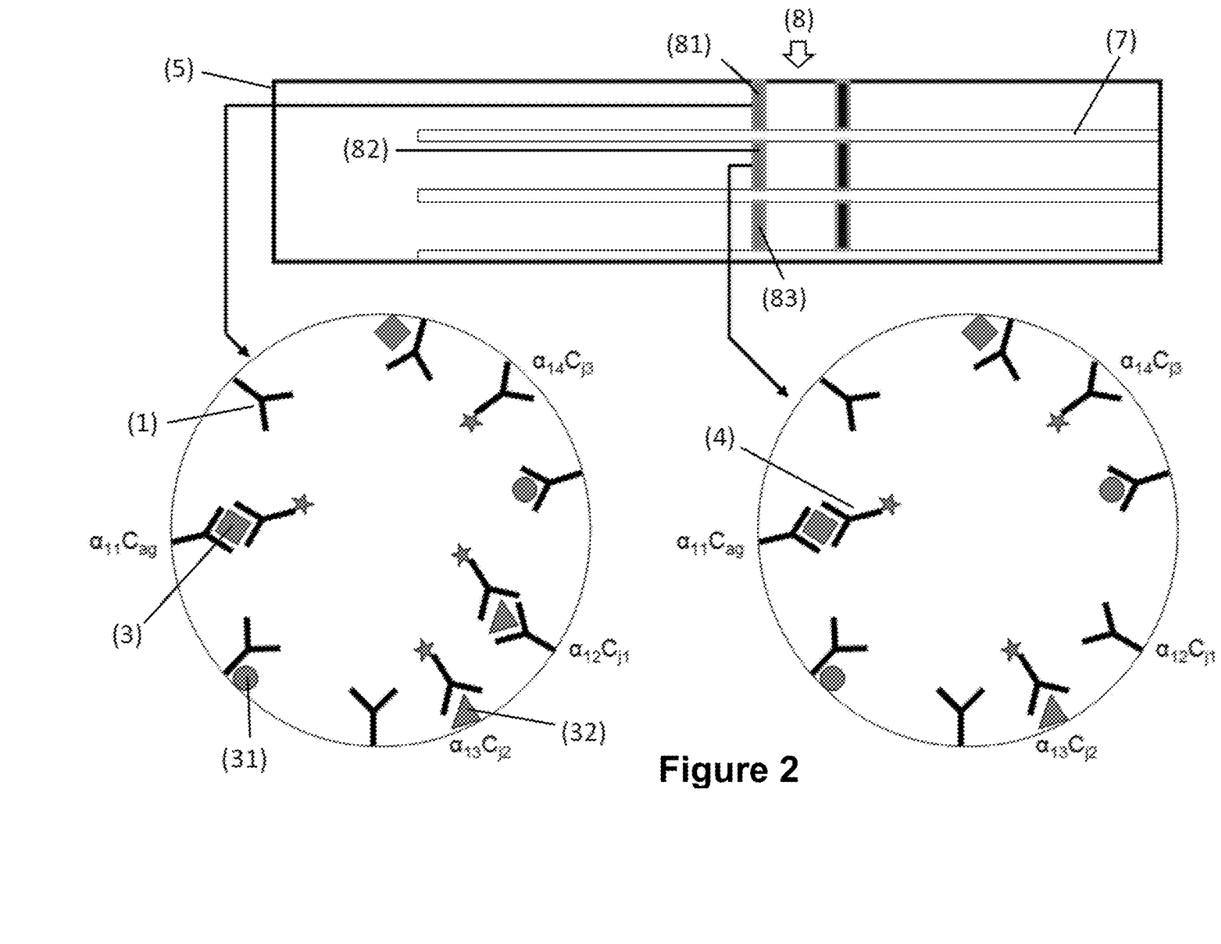
FIG. 2: An illustration of the multisite lateral flow system and the components in the detected signal. The two schematics on the bottom correspond to two of the sites.

A biosensor providing a multiple site testing platform was described in US Published Patent Application US 2011/0091870, wherein the multiple sites in the biosensor could be subjected to different reaction conditions to modulate the binding of the biomolecular analyte (for example proteins) to the probe molecule. For example the signal detected in a biosensor having four sites also can have several components e.g four. These four terms correspond to for example the concentration of the biomarker of interest, the concentration of analytes in the sample that bind non-specifically to primary antibody sites and prevent the biomarker to bind, the concentration of the analytes in the sample that form a sandwich and produce a false signal, and finally the concentration of the analytes in the sample that physisorb to the surface and produce a false signal. Each term is also proportional to a binding efficiency factor, $\alpha_{ij}$, which is a function of the molecular affinity and other assay conditions, e.g., flow speed. By controlling the condition in each site separately, different sites will exhibit different efficiency factors. Accurate measurement of the signal at each site will result in multiple equations and multiple unknowns—for example:

$$\begin{cases} S_1 = \alpha_{11}C_{ag} - \alpha_{12}C_{j1} + \alpha_{13}C_{j2} + \alpha_{14}C_{j3} \\ S_2 = \alpha_{21}C_{ag} - \alpha_{22}C_{j1} + \alpha_{23}C_{j2} + \alpha_{24}C_{j3} \\ S_3 = \alpha_{31}C_{ag} - \alpha_{32}C_{j1} + \alpha_{33}C_{j2} + \alpha_{34}C_{j3} \\ S_4 = \alpha_{41}C_{ag} - \alpha_{42}C_{j1} + \alpha_{43}C_{j2} + \alpha_{44}C_{j3} \end{cases} \Rightarrow C_{ag}$$

where $C_{ag}$ corresponds to the targeted biomolecular analyte concentration and $C_{j1}$, $C_{j2}$, $C_{j3}$ correspond to the total concentration of molecules which result in different terms in background signal, as shown in FIG. 2.

Accurate control of assay conditions at different sites, which allows large changes in the binding efficiency factors, results in an array of data from which a quantitative or more accurate qualitative determination of the biomolecular analyte of interests can be obtained. In addition, using electrical and electrochemical detection on a lateral flow assay device could significantly improve current point of care diagnostics.

SUMMARY OF THE INVENTION

Herein is provided a lateral flow assay device having a multisite array of test sites, the device comprising at least one electrode, wherein each electrode can comprise an actuation element and/or a sensing element. Such lateral flow assay device can provide for the control of one or more parameters which affect the signal intensity of a biomolecular analyte of interest in a sample and measure the signal intensity of the biomolecular analyte of interest in order to determine its concentration in the sample. Such integrated electrodes in a lateral flow assay device can control local environment parameters such as for example pH, temperature, and ionic concentration, but also measure such parameters which include for example the flow rate, flow shape, temperature or ionic concentration of a sample when flowing across the device. This lateral flow assay device can also measure a signal from the biomolecular analyte of interest at each site in the multisite array in order to determine its concentration in the sample.

In one embodiment there is provided a lateral flow assay device comprising a multisite array of test sites for measuring a biomolecule analyte having a solid support including absorbent material for providing capillary flow comprising:
  a) a sample portion for receiving a sample;
  b) a diagnostic portion comprising a multisite array of test sites each comprising a probe for the biomolecular analyte, wherein at each test site of the multisite array the conditions for the interaction between the biomolecular analyte and the probe can be varied independently;
  c) an absorbent portion of absorbent material for providing capillary flow; and
  d) at least one electrode,
wherein the sample portion, diagnostic portion, and absorbent portion are in capillary flow communication resulting in a capillary flow from sample portion a) towards absorbent portion c), whereby the sample flows across the probe at each test site in the diagnostic portion to provide contact between the sample and such probe.

The biosensor in the form of a lateral assay device described herein can be integrated with for example a CMOS, electrode array, or TFT based biosensor to generate changes in binding efficiencies between test sites in the later flow assay device having an array of multiple test sites. In addition, at least one electrode in the LF assay device is connected to a processing unit for computing one or more parameters relating to the sample and/or biomolecular analyte of interest. The parameter(s) that are computed are those that affect the intensity of the signal from the bound labeled-biomolecular analyte complex, thereby affecting the computation of the concentration of the analyte in the sample. Thus, the integrated electrodes in the LF assay device not only modulates the pH, ionic concentration, and/or temperature at the local environment of the test sites but can also measure other parameters which affect the accurate determination of the concentration of a biomolecular analyte of interest in the sample such as for example flow rate and flow shape of the sample across the diagnostic portion of the LF assay device.

In another embodiment there is provided a lateral flow assay device comprising a multisite array of test sites for measuring a biomolecule analyte having a solid support including absorbent material for providing capillary flow and being divided into parallel lanes in the flow direction, comprising:
  a) a sample portion for receiving a sample;
  b) a diagnostic portion comprising a multisite array of test sites each comprising a probe for the biomolecular analyte, wherein at each test site of the multisite array the conditions for the interaction between the biomolecular analyte and the probe can be varied independently;
  c) an absorbent portion of absorbent material for providing capillary flow;
  d) at least one electrode as an actuation element; and
  e) at least one electrode as an sensing element,
wherein the sample portion, diagnostic portion, and absorbent portion are in capillary flow communication resulting in a capillary flow from sample portion a) towards absorbent portion c), whereby the sample flows across the probe at each test site in the diagnostic portion to provide contact between the sample and such probe.

In yet another embodiment there is provided a method for determining the concentration of a biomolecule analyte in a biological sample, the method comprising:
  a) providing a lateral flow assay device comprising a multisite array of test sites in which the conditions for interacting with a biomolecule analyte can be varied independently, the lateral flow device having a solid support including absorbent material for providing capillary flow comprising a sample portion for receiving a sample, a diagnostic portion comprising the multisite array of test sites, an absorbent portion of absorbent material for providing capillary flow, at least one electrode as an actuation element, and at least one electrode as an sensing element;
  b) adding a biological sample to the sample portion of the lateral assay device, whereby the sample flows across a probe at each test site in the diagnostic portion to provide contact between the sample and such probe;
  c) obtaining a signal from each sensing element at each test site following contact between the sample and the probe;
  d) obtaining, if present, a signal from each sensing element not located at a test site; and
  e) determining the concentration of the biomolecular analyte from the signals obtained in steps c) and d),
wherein activation of each actuation element varies at least one local environment parameter at each test site.

The concentration of the biomolecular analyte in the sample is computed by determining the signal intensity of the biomolecular analyte bound to the diagnostic portion of the lateral flow assay device and taking in consideration one or more of the parameters that were determined for the sample flowing across the diagnostic portion of the lateral flow immunoassay device.

BRIEF DESCRIPTION OF THE FIGURES

FIG. 5: An illustrative example of a multisite lateral flow system consisting of: (11) an area printed with buffer salts to alter the pH (e.g. pH 5), or an area to alter the temperature (e.g. 40 degrees), or an area printed with sodium chloride to alter the ionic concentration (e.g. 250 mM); (12) an area printed with buffer salts to alter the pH (e.g. pH 6), or an area to alter the temperature (e.g. 30 degrees), or an area printed with sodium chloride to alter the ionic concentration (e.g. 500 mM); (13) an area printed with buffer salts to alter the pH (e.g. pH 7), or an area to alter the temperature (e.g. 30 degrees), or an area printed with sodium chloride to alter the ionic concentration (e.g. 750 mM); (7) a region on the lateral flow patterned to confine the fluid to prevent lateral cross mixing between the channels, an example may include a material barrier, solid, hydrophobic; (15) test and control lines; and (16) sensing areas for determining physiological parameters (e.g. Temperature, pH, ionic concentration, flow profile, analyte concentration). In which n is representative for an $n^{th}$ area printed with single or multiple areas of buffer salts, to alter the pH (e.g. pH 1-12), or an area to alter the temperature (e.g. 0-120 degrees), or an area printed with sodium chloride to alter the ionic concentration (e.g. 50-5000 mM), or areas with sensing elements to determine physiological parameters, or a combination of the aforementioned areas.

DETAILED DESCRIPTION

Electrical sensors can be integrated into Lateral Flow (LF) assay devices for modulating local environment parameters or conditions and/or determining measurable parameters of a sample, which parameters affect the accuracy for measuring the concentration of a biomolecular analyte of interest in such sample. Different kinds of printed electrical sensors can be integrated into a Lateral Flow assay device (flow speed sensor, flow shape sensor, temperature sensor) as also described in U.S. patent application Ser. No. 13/658,614, which application is incorporated herein by reference in its entirety. Nearly every printing process can be used to print these conductive electrodes for example screen-printing, gravure printing or inkjet-printing but also spraying or brushing techniques. The materials for these electrical sensors include for example silver, platinum, carbon, copper or gold inks or pastes.

Since some of the solvents of conductive materials can attack the membranes (especially nitrocellulose) used in the diagnostic portions of the LF assay device, the electrodes can also be applied on different parts of the device, such as for e.g. bellow the nitrocellulose membrane on the backing-access through the backing. For example, certain alternatives for integrating a printed electrode actuation element or sensing element in a LF assay device are indicated as in FIG. 3. These include printing of the electrode on a backing or support material below the membrane, wherein the electrode may be accessed through the backing or solid support material. Alternatively, the electrodes are printed on the diagnostic portion (the diagnostic membrane) or in gaps of such diagnostic portion of the LF assay device. In another alternative, the electrodes are not printed electrodes but comprise non-printed electrodes applied to or through one or more of the various portions of the LF assay device. Printing of the electrode can be on any one of the sample portion, diagnostic portion, and/or absorbent portion of the solid support. Preferably, the electrodes are printed on the diagnostic portion of the device which contains the binder material for interaction with the analyte. Alternatively, the applied electrodes are non-printed electrodes.

As such there is provided a lateral flow assay device comprising a multisite array of test sites for measuring a biomolecule analyte having a solid support including absorbent material for providing capillary flow comprising:
  a) a sample portion for receiving a sample;
  b) a diagnostic portion comprising a multisite array of test sites each comprising a probe for the biomolecular analyte, wherein at each test site of the multisite array the conditions for the interaction between the biomolecular analyte and the probe can be varied independently;
  c) an absorbent portion of absorbent material for providing capillary flow; and
  d) at least one electrode,
wherein the sample portion, diagnostic portion, and absorbent portion are in capillary flow communication resulting in a capillary flow from sample portion a) towards absorbent portion c), whereby the sample flows across the probe at each test site in the diagnostic portion to provide contact between the sample and such probe. Binding of the analyte in the sample (and the conjugate) to the binder, located on a test-line or test-site of the diagnostic portion, will result in a signal being generated at that location. The intensity of the signal being generated is an indication of the concentration of the biomolecular analyte of interest in the sample applied to the sample portion of the device. Collecting such signal data from multiple test sites wherein the local environmental parameters which affect the interaction between the biomolecular analyte of interest in the sample and the binder at the test-line or test-site are varied in a controlled manner provides a more accurate measurement for computing the concentration biomolecular analyte in the sample.

In such a device the sample portion, the conjugate portion (if present), the diagnostic portion, and the absorbent portion can be placed on a single solid support or backing material. This solid support or backing material may be flexible but is inert and provides sufficient support to maintain a capillary flow of the sample through the various portions that are of absorbent material.

The diagnostic portion of the LF assay device may be prepared using a membrane. Such diagnostic membrane can for example be selected from a nitrocellulose membrane, a polyvinylidene fluoride membrane, a nylon membrane that is optionally charge modified, and a polyethersulfone membrane. The diagnostic membrane further comprises an immobilized binder for the analyte. Such binder can be any molecule or bio-molecule with which the biomolecular analyte of interacts so as to result in a binder-analyte/ligand complex that is immobilized onto the diagnostic membrane. Examples of such binders may be an antibody, antigen, protein, enzyme or part thereof, substrate or part thereof, peptide, DNA, or RNA.

The pH, temperature, and salt concentrations present when a probe/biomolecular analyte complex (ligand complex) is formed or is washed have a significant effect on the dissociation constant ($K_d$) of the ligand complex. Variations in the dissociation constant for a particular interaction results in changes in the binding efficiency of an analyte to form ligand complexes at a test-line or test-site from which a signal can be obtained. By integrating a series of pH, temperature, and/or salt modification elements, multiple binding conditions can be probed on a single lateral flow device to improve measurement quality.

In order to vary the pH or ionic (salt) concentration in a multisite array of test sites in a LF assay device as provided herein a method as described in U.S. patent application Ser. No. 13/543,300, which application is incorporated herein by reference in its entirety, can be used wherein is described varying such local environmental parameters which affect binding between a biomolecular analyte of interest and a diagnostic portion of the LF assay device in a biosensor. In short such method of modulating the pH or ionic concentration comprises providing an electrode as an actuation element in the LF assay device, adding an electrochemically active agent, an enzyme, an enzyme substrate, a buffer inhibitor, or a combination thereof to the sample solution or from a separate reservoir which is in contact with the membrane in the LF assay device which is engaged when the sample is flow across the membrane of the LF assay device, and reacting the electrochemically active agent, the enzyme, the enzyme substrate, or a combination thereof in at the test-site to produce H+ ion or OH− ions, or increasing the diffusion of H+ ions or OH− ions with the buffering agent or inhibiting the interaction between H+ ions or OH− ions and buffering salts with the buffer inhibitor.

Figure 5:
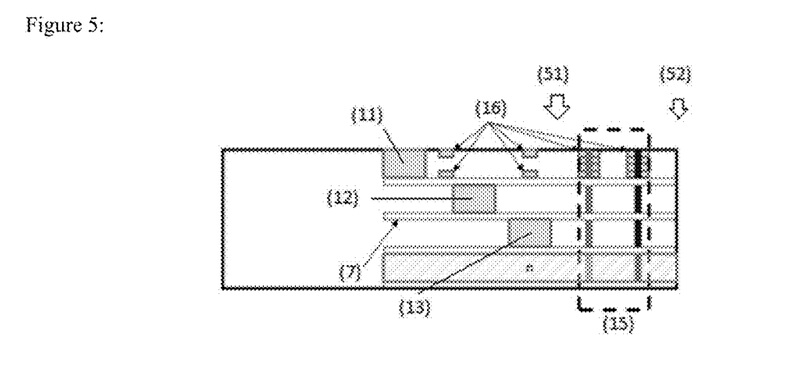
Figure 6:
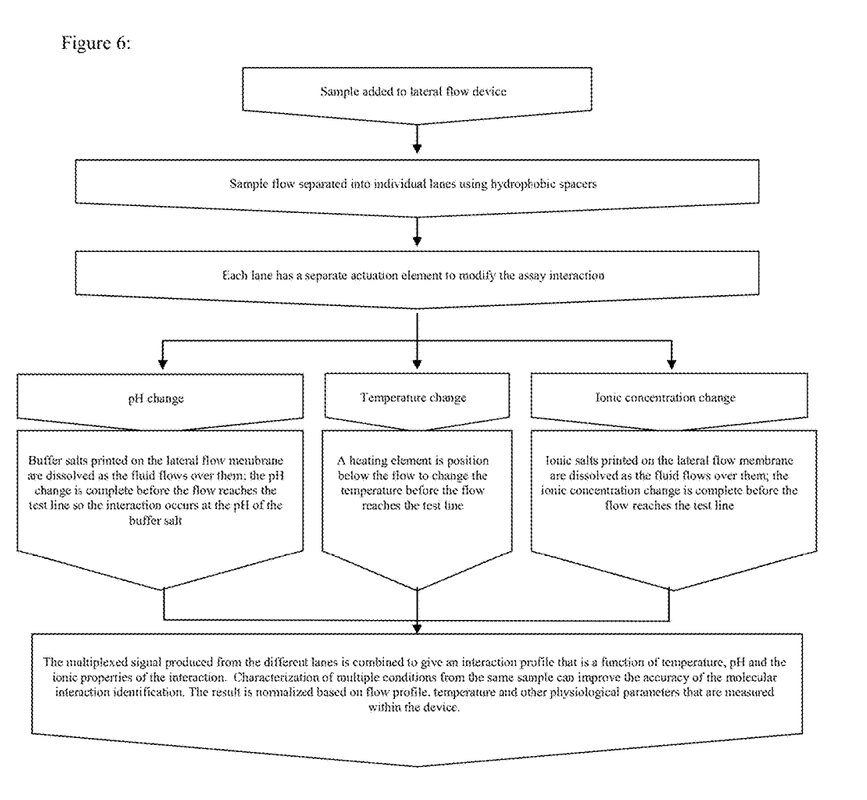
FIG. 6: A flow chart illustrating the experimental process flow.

Thus, ionic concentrations can be changed in the LF assay device using electrode and or enzymes, but also using printed salts or salt-embedded beads. Specifically an electrode can be activated under faradaic or non-faradaic conditions to generate H+ or OH− ions at specific regions of the lateral flow device. For example, enzymes can be printed on the surface to produce H⁺ as a byproduct of the enzymatic oxidation reaction as described in U.S. patent application Ser. No. 13/543,300. Alternatively ionic salts or beads embedded with ionic salts can be printed onto the nitrocellulose membrane in the LF assay device to create zones of variable ionic concentration. FIG. 5 illustrates a potential device with 3 zones where the ionic concentration (including [H⁺]) is altered on a per-channel basis. The area is depicted as "n" to represent that the position of these zones is variable. Actuation elements (11), (12), and (13) illustrate one example of where the zones may be located, but in practice, they can be positioned anywhere before, after, or on the test or control lines. The number and distribution of such zones is not limited to that depicted in the figure; and a single channel can encompass multiple zones.

In the above described method a pH or ionic concentration gradient can be obtained at the various test sites in a multisite array LF assay device. The variation of the local pH and/or ionic concentration in the vicinity of the probe, over subsets of the multisite array of the LF assay device, allows for modulating the binding efficiency of the probe and a biomolecular analyte to be tested from a biological sample. The biomolecular analyte of interest, when bound to the probe, can be then detected using a detection agent, such as for example a labeled secondary antibody as in a Lateral Flow Immunoassay device. The modulation of binding efficiencies in a subset of a multisite array provides a method for the accurate determination of such analyte of interest.

A multisite array of test sites as in the LF assay device described herein preferably includes a number of different subarrays/subsets of test sites. Each test sites represents a site for performing an analysis of a (biomolecular) analyte from a biological sample through the detection of the (biomolecular) analyte using a (biomolecular) probe. The local environment/analytical conditions in each test site in each of the subarrays/subsets may be varied to obtain a collection of varied signals that will result in multiple equations and multiple unknowns from which the concentration of the (biomolecular) analyte can be determined in order to obtain an accurate measurement of the (biomolecular) analyte.

The multiple unknowns in the obtained varied signals each includes a term that is proportional to a binding efficiency factor, $\alpha_{ij}$, and the concentrations of the various molecules in the biological sample binding that are detected at the test site. The multiple equations with multiple unknowns may be represented for example as follows, $$\begin{cases} S_1 = \alpha_{11}C_{ag} - \alpha_{12}C_{j1} + \alpha_{13}C_{j2} + \alpha_{14}C_{j3} \\ S_2 = \alpha_{21}C_{ag} - \alpha_{22}C_{j1} + \alpha_{23}C_{j2} + \alpha_{24}C_{j3} \\ S_3 = \alpha_{31}C_{ag} - \alpha_{32}C_{j1} + \alpha_{33}C_{j2} + \alpha_{34}C_{j3} \\ S_4 = \alpha_{41}C_{ag} - \alpha_{42}C_{j1} + \alpha_{43}C_{j2} + \alpha_{44}C_{j3} \end{cases} \Rightarrow C_{ag}$$

where $C_{ag}$ corresponds to the targeted biomolecular analyte concentration and $C_{j1}$, $C_{j2}$, $C_{j3}$ correspond to the total concentration of molecules which result in different terms in background signal, from which collection of multiple equations the concentration of the targeted biomolecular analyte can be determined.

The number of subarrays/subsets, as well as the number of test sites within each subarray/subset may be varied, as needed to obtain such accurate measurement of the biomolecular analyte. Some of these analytical conditions also include parameters such as for example temperature. For example the temperature at the test-site in which the biomolecular probe and analyte of interest in the biological sample interact can be varied using electromagnetic heat at the test-site.

The samples for use in the LF assay device can be human-derived, such as blood, lymph, serum, saliva, biological cells, and urine, or non-human fluid samples such as (but not limited to) surface water, foodstuffs, and biological samples.

The biomolecular analytes of which the concentration in a sample can be determined with the LF assay device include for example biological molecules, cells, toxicity biomarkers, bacterial biomarkers, hormones, viruses and their fragments, and small molecules or antigens; specifically: vitamins (A, B1, B2, B3, B5, B6, B7, B9, B12, C, D, E, K), cytokines (IFNγ, IL-2, IL-4, IL-5, IL-7, IL-9, IL-10, IL-12 IL-15, IL-21, IL-22 IL-23, TGFβ, TNFβ, MCP-1), Autoantibodies, IgG, IgA, IgE, and IgM and subclasses of these molecules, metalloproteinase, chemokines, bacterial toxins, heavy metals, and chemotherapy agents.

For electrical detection, both pure electrical and electrochemical detection can be integrated; more specifically capacitive, resistive, impedance, faradaic, non-faradaic, and redox detection methods can be used. As such at least one electrode in the LF assay device comprises a sensing element. In the multisite array of test-sites of the LF assay device such sensing element in the form of an electrode or pair of electrodes can be located at each test-site. Detection and amplification methods can additionally be supplemented by optical, enzymatic, colorimetric, magnetic, absorption, fluorescence and chemiluminescence methods.

By integrating a series of electrodes patterned onto the lateral flow assay device, the flow speed and the flow profile of a sample can also be determined, as described in U.S. patent application Ser. No. 13/658,614 (which is incorporated herein in its entirety by reference). As described therein at least one electrode pair positioned upstream of the test-site in the direction of the capillary flow and at least one electrode pair positioned at or downstream of the test-site in the direction of the capillary flow provides signals from which the flow speed (flow rate) at the test-site can be determined. When an array of such electrode pairs is positioned across the LF assay device perpendicular to the capillary flow the signals obtained can provide a measurement of the flow-shape of the capillary flow.

Temperature measurements can be integrated using a conductive material that changes resistivity as a function of temperature. This readout can be used as a data point to ensure that measurements are acquired at optimal times and temperatures. Simultaneously, temperature values can be used to normalize measurements for comparison to other samples acquired under different conditions.

Temperature control in lateral flow systems can be initiated via a heating block or infrared radiation source, both of which are readily multiplexed. FIG. 5 illustrates a potential device with 3 zones where temperature is independently adjustable to affect fluid flowing over nearby test and control lines. The area is depicted as "n" to signify that the position of the temperature zone is variable. Positions for actuation elements (11), (12), and (13) illustrate one example of where the zones may be located, but in practice, they can be positioned anywhere before, after, or on the test or control lines. The number and distribution of temperature zones is also not limited to that depicted in the figure; a single channel can encompass multiple zones.

In another embodiment there is provided A lateral flow assay device comprising a multisite array of test sites for measuring a biomolecule analyte having a solid support including absorbent material for providing capillary flow and being divided into parallel lanes in the flow direction, comprising:
- a) a sample portion for receiving a sample;
- b) a diagnostic portion comprising a multisite array of test sites each comprising a probe for the biomolecular analyte, wherein at each test site of the multisite array the conditions for the interaction between the biomolecular analyte and the probe can be varied independently;
- c) an absorbent portion of absorbent material for providing capillary flow;
- d) at least one electrode as an actuation element; and
- e) at least one electrode as an sensing element, wherein the sample portion, diagnostic portion, and absorbent portion are in capillary flow communication resulting in a capillary flow from sample portion a) towards absorbent portion c), whereby the sample flows across the probe at each test site in the diagnostic portion to provide contact between the sample and such probe.

The LF assay device can be used in a method of determining the concentration of a biomolecular analyte in a sample. Such sample can be human-derived, such as blood, lymph, serum, saliva, biological cells, and urine, or non-human fluid samples such as (but not limited to) surface water, foodstuffs, and biological samples. The presence of a multisite-array of testing-sites in the LF assay device allows for the generation of a multiple signals at different environmental conditions from which the concentration of a biomolecular analyte of interest can be more accurately computed.

As such, in yet another embodiment there is provided A method for determining the concentration of a biomolecular analyte in a biological sample, the method comprising:
- a) providing a lateral flow assay device comprising a multisite array of test sites in which the conditions for interacting with a biomolecular analyte can be varied independently, the lateral flow device having a solid support including absorbent material for providing capillary flow comprising a sample portion for receiving a sample, a diagnostic portion comprising the multisite array of test sites, an absorbent portion of absorbent material for providing capillary flow, at least one electrode as an actuation element, and at least one electrode as an sensing element;
- b) adding a biological sample to the sample portion of the lateral assay device, whereby the sample flows across a probe at each test site in the diagnostic portion to provide contact between the sample and such probe;
- c) obtaining a signal from each sensing element at each test site following contact between the sample and the probe;
- d) obtaining, if present, a signal from each sensing element not located at a test site; and
- e) determining the concentration of the biomolecular analyte from the signals obtained in steps c) and d), wherein activation of each actuation element varies at least one local environment parameter at each test site.

The concentration of the biomolecular analyte in the sample is computed by determining the signal intensity of the biomolecular analyte bound to the diagnostic portion of the lateral flow assay device and taking in consideration one or more of the parameters that were determined for the sample flowing across the diagnostic portion of the lateral flow immunoassay device.

The following figures provide some aspects of the LF assay device as described herein. The invention described herein however is not limited to these illustrative figures. In FIG. 1 an example is provided of cross-reactivity which frequently is an issue when accurately determining the concentration of a biomolecular analyte in a sample. In this example a primary antibody used as probe (1) is immobilized on a solid support or membrane (2). The biomolecular analyte or antigen (3) is recognized by the primary antibody (1) and would interact/bind with such immobilized probe or binder in the form of a primary antibody (1). In this example a labeled secondary antibody or conjugate (4) recognizes the biomolecular analyte or antigen (2) and interact with it to provide a measurable signal at the test-site, as in FIG. 1*a*. In FIG. 1*b* cross-reactivity occurs between the immobilized probe or primary antibody (1) and other analytes (31 and 32) in the biological sample. These other analytes (31 and 32) may bind to the probe or primary antibody (1) and prevent interaction with the biomolecular analyte of interest or antigen (3) or they may interact with the labeled secondary antibody (4) thereby causing measurable signals being obtained that do not related to the biomolecular analyte of interest (3) in the biological sample. Therefore the obtained signals are not an accurate reflection of the amount biomolecular analyte (3) in the biological sample at the test-site and thus result in an inaccurate measurement of the concentration of the biomolecular analyte (3) in the biological sample.

The lateral flow assay device described herein provides a means for more accurately determining the concentration of the biomolecular analyte (3) in a biological sample. The LF assay device comprises a solid support (5), as depicted in FIG. 2, which supports a sample portion, a diagnostic portion, and an absorbent portion. This LF assay device may comprise a multisite array of test-sites (8) which may be separated by one or more spacers (7). Each test-site (81, 82, and 83) may have differences in local environmental parameters which affect interaction between the biomolecular analyte (3), the other analytes (31 and 32) and the probe or primary antibody (1) and the labeled secondary antibody (4). As a result the binding efficiency at each testing-site varies for each analyte giving rise to different signals. Calculation of the concentration of the biomolecular analyte (3) of interest can be more accurately determined using the various signals obtained taking in consideration the variations in binding efficiency for the different analytes due to variations in local environmental parameters.

Figure 3:
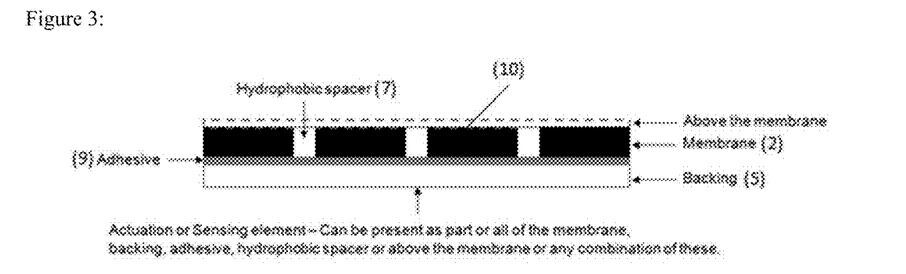
FIG. 3: An illustration of the cross section of a lateral flow device. The electrode, actuation or sensing element may be a part of the backing, adhesive, membrane, or above the membrane and/or a combination of these.
Figure 4:
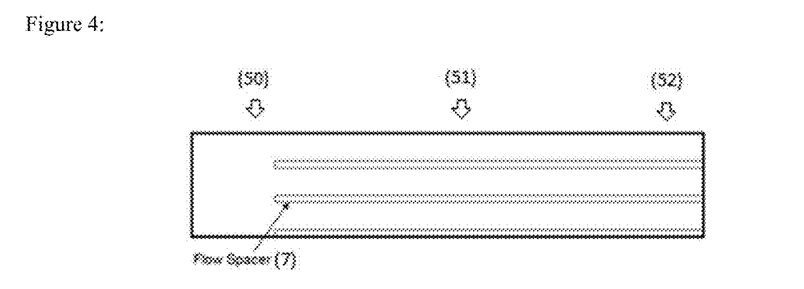
FIG. 4: An illustration of a patterned lateral flow device with a series of controlled fluid channels to prevent lateral cross mixing between the channels.

The at least one electrode can be integrated on the LF assay device in various ways, as in FIG. 3. On the solid support (5) or backing an adhesive layer (9) may be applied onto which a membrane (2) of for example the diagnostic portion of the LF assay device may be applied. The membrane (2) of the diagnostic portion may be divided into separate lanes by using a spacer (7), which is preferably hydrophobic. The electrode(s) (10) in the form of an actuation element or sensing element can be present as part of the membrane (2), positioned in gaps therein, or above the membrane or below the membrane, and/or a combination thereof. The electrode(s) may also be present on the backing or solid support portion (5) of the LF assay device. Such a separation of the LF assay device in separate lanes is shown in FIG. 4 wherein the lanes are divided by spacers (7), which are preferably hydrophobic. The lanes may run across the entire length of the sample portion (50), diagnostic portion (51), and absorbent portion (52) of the LF assay device in the direction of the capillary flow, or only partially dissecting such portions of the LF assay device.

A LF assay device wherein at least the diagnostic portion (51) and the absorbent portion (52) are divided with spacers (7) into separate lanes is shown in FIG. 5. At various positions in various lanes actuation elements (11-13) can be present in such a separate lane. The actuation elements (11-13), which may be in the form of an electrode, control at least one local environmental parameter which affects the interaction of analytes in the sample with the binder at the testing-site. From the sensing elements (16), which may be in the form of an electrode or electrode pair, a measurable signal can be obtained. These sensing elements (16) can be placed anywhere in each lane or at the testing-sites (15) in each lane, which testing-sites (15) may contain a multisite array of testing-sites. Each lane may contain one or more of such testing-sites (15). From the multiple measurable signals obtained from the various testing-sites on the LF assay device the concentration of the biomolecular analyte of interest can be computed.

The invention described herein has certain advantages over conventional lateral flow assay devices in that the electrodes can collect data in real-time, which can reduce the duration of an experiment. This has the advantage of revealing transient signal changes, which can be used to improve the accuracy of the result from the additional data gathered. In addition, electronic sensing is built upon well-developed, scalable, and standardized industrial processes. It significantly reduces engineering and material complexities associated with optical sensing modalities. However, the most important advantage is that the LF device and method described herein can more accurately determine the concentration of a biomolecular analyte in a sample through reduction of effect of non-specific signals and other environmental parameters on the determination of the concentration of the biomolecular analyte of interest.

The invention claimed is:

1. A lateral flow assay device comprising:
   a) a solid support;
   b) a sample portion for receiving a sample;
   c) a diagnostic portion comprising multiple parallel lanes and one or more spacer elements, wherein each of the lanes is separated from a respective adjacent lane by a respective spacer element, each of the lanes comprises one or more respective test sites distinct from the one or more test sites of the other lanes, and each of the test sites comprises an immobilized probe for interacting with a biomolecular analyte;
   d) an absorbent portion of absorbent material for providing capillary flow;
   e) at least one electrode as an actuation element applied in each of the lanes on the diagnostic portion; and
   f) at least one electrode as a sensing element applied in each of the lanes on the diagnostic portion;
   wherein:
      the sample portion, diagnostic portion, and absorbent portion are on the solid support and in capillary flow communication resulting in a capillary flow from the sample portion towards the absorbent portion, whereby the sample flows across the probe at each of the test sites in the diagnostic portion to provide contact between the sample and the probe of the respective test site;
      the multiple lanes are parallel to the direction of capillary flow;
      within each of the lanes, at each of the test sites, the respective at least one actuation element electrode is configured to control and independently vary a local environmental parameter for interaction between the biomolecular analyte and the respective probe of the respective test site;
      the local environmental parameter is a parameter selected from pH, temperature, and ionic concentration; and
      within each of the lanes, at each of the test sites, the respective at least one sensing element electrode is configured to determine at least one measurable environmental parameter of the sample and comprises a series of multiple electrode pairs arranged side-by-side across the flow path of the sample perpendicular to the capillary flow.

2. The device of claim 1, further comprising upstream of the diagnostic portion in the direction of the capillary flow a conjugate portion comprising particulate material.

3. The device of claim 1, wherein the probe is a binder for the biomolecular analyte.

4. The device of claim 1, wherein the at least one measurable environmental parameter is selected from sample flow rate, sample flow shape, temperature, ionic concentration, and pH.

5. The device of claim 1, wherein the sample portion is divided, parallel to the direction of capillary flow, into multiple lanes, and each of the lanes of the sample portion is separated from a respective adjacent lane of the sample portion by the respective spacer element, such that the lanes of the sample portion are continuous with the lanes of the diagnostic portion.

6. The device of claim 1 wherein the spacer element is a hydrophobic spacer element.

7. The device of claim 1, wherein each lane comprises multiple actuation element electrodes configured to control the local environmental parameter.

8. The device of claim 1, wherein the one or more testing sites each comprises multiple actuation element electrodes configured to control the local environmental parameter.

9. The device of claim 5, wherein each lane of the sample portion comprises one or more sensing elements for determining a measurable parameter of the sample and/or biomolecular analyte.

10. The device of claim 9, wherein the measurable parameter is a parameter selected from sample flow rate, sample flow shape, temperature, ionic concentration, and pH.

11. The device of claim 1, wherein the diagnostic portion comprises a membrane selected from a nitrocellulose membrane, a polyvinylidene fluoride membrane, a nylon membrane that is optionally charge modified, and a polyethersulfone membrane.

12. The device of claim 1, wherein the at least one sensing element electrode comprises two electrode pairs to determine the flow rate of the sample across the diagnostic portion of the lateral flow immunoassay device.

13. The device of claim 4, wherein the at least one measurable environmental parameter is the flow shape of the sample across the diagnostic portion of the lateral flow device.

14. The device of claim 1, wherein the at least one electrode as a sensing element comprises a defined structure of conductive material configured to determine the temperature of the sample flowing across the diagnostic portion of the lateral flow device, wherein the conductive material changes resistivity in a defined temperature range.

15. The device of claim 1, wherein the at least one electrode as an actuation element and the at least one electrode as a sensing element are printed in the lanes of the diagnostic portion.

16. The device of claim 1, wherein the at least one electrode as a sensing element is connected to a processing unit for computing the at least one measurable environmental parameter of the sample.

17. The device of claim 16, wherein the at least one measurable environmental parameter of the sample is selected from sample flow rate, sample flow shape, temperature, and concentration of the biomolecular analyte.

18. A method for determining the concentration of a biomolecular analyte in a biological sample, the method comprising:
  a) providing a lateral flow assay device comprising:
    a solid support;
    a sample portion for receiving a sample;
    a diagnostic portion comprising multiple parallel lanes and one or more spacer elements, wherein each of the lanes is separated from an adjacent lane by a respective spacer element, each of the lanes comprises one or more respective test sites distinct from the one or more test sites of the other lanes, and each of the test sites comprises an immobilized probe for interacting with the biomolecular analyte;
    an absorbent portion of absorbent material for providing capillary flow;
    at least one electrode as an actuation element applied in each of the lanes on the diagnostic portion; and
    at least one electrode as a sensing element applied in each of the lanes on the diagnostic portion;
  b) applying a biological sample to the sample portion of the lateral assay device, whereby the sample flows across the immobilized probe at each of the test sites in the diagnostic portion to provide contact between the sample and the immobilized probe of the respective test site;
  c) obtaining a signal from each sensing element at each of the test sites following contact between the sample and the respective immobilized probe;
  d) obtaining, if present, a signal from each sensing element not located at any of the test sites; and
  e) determining the concentration of the biomolecular analyte from the signals obtained in steps c) and d);
  wherein:
    the multiple lanes are parallel to the direction of capillary flow;
    at each of the test sites, activation of the respective actuation element varies at least one respective local environmental parameter for interaction between the biomolecular analyte and the probe of the respective test site;
    the local environmental parameter is at least one of: a temperature of the sample at the diagnostic portion, a pH of the sample at the diagnostic portion, and an ionic concentration of the sample at the diagnostic portion; and
    at each of the test sites, the respective sensing element determines at least one measurable environmental parameter of the sample and comprises a series of multiple electrode pairs arranged side-by-side across the flow path of the sample perpendicular to the capillary flow.

19. The method of claim 18, wherein the at least one electrode as actuation element and the at least one electrode as sensing element are connected to a processing unit comprising a display.

* * * * *